United States Patent [19]

Hunt et al.

[11] Patent Number: 4,873,984
[45] Date of Patent: Oct. 17, 1989

[54] TECHNIQUES FOR CALCULATING ULTRASONIC INTEGRATED BACKSCATTER USING FREQUENCY OR TIME DOMAIN TECHNIQUES

[75] Inventors: Thomas J. Hunt, Derry, N.H.; James G. Miller, Clayton, Mo.; Lewis J. Thomas, III, Schenectady, N.Y.; Hewlett E. Melton, Jr., Andover; Thomas A. Shoup, Lowell, both of Mass.

[73] Assignee: Hewlett-Packard Company, Palo Alto, Calif.

[21] Appl. No.: 869,502

[22] Filed: May 30, 1986

[51] Int. Cl.⁴ .............................................. A61B 10/00
[52] U.S. Cl. ................... 128/660.07; 73/602
[58] Field of Search ............... 128/660, 661, 660.06, 128/660.07, 660.01; 73/599, 625, 626, 631, 602

[56] References Cited

U.S. PATENT DOCUMENTS

| 4,016,750 | 4/1977 | Green | 73/631 X |
| 4,043,181 | 8/1977 | Nigani | 73/631 X |
| 4,414,850 | 11/1983 | Miwa et al. | 73/599 |
| 4,452,082 | 6/1984 | Miwa | 73/599 |
| 4,470,303 | 9/1984 | O'Donnell | 73/602 |
| 4,662,380 | 5/1987 | Riley | 73/631 X |

OTHER PUBLICATIONS

Perey, J. E. et al., "Applicability of UTS Tissue Characterization for Longitudinal Assessment and Differentiation of Calcification and Fibrosis in Cardiomyopathy" JACC vol. 4, No. 1, Jul. 1984, pp. 88-95.
Shing, K. K. et al., "Scattering of UTS by Blood", IEEE BME Trans. vol. 23, #6, Nov. 1976, pp. 460-467.

*Primary Examiner*—Francis J. Jaworski
*Attorney, Agent, or Firm*—Donald N. Timbie; Frank R. Perillo

[57] ABSTRACT

Apparatus for deriving signals indicating a condition of tissue within an area by launching spaced supersonic pulses into a body under examination and detecting the power of supersonic waves scattered from locations along a plurality of known paths. Gain control elements are provided for compensating for changes in amplitude of the scattered supersonic waves resulting from their passage through blood or tissue, the increased attenuation with frequency of the spectrum of the launched pulses and the focussing of the launched pulses. Compensation for ring-down and the attenuation of the chest wall is also provided.

7 Claims, 3 Drawing Sheets

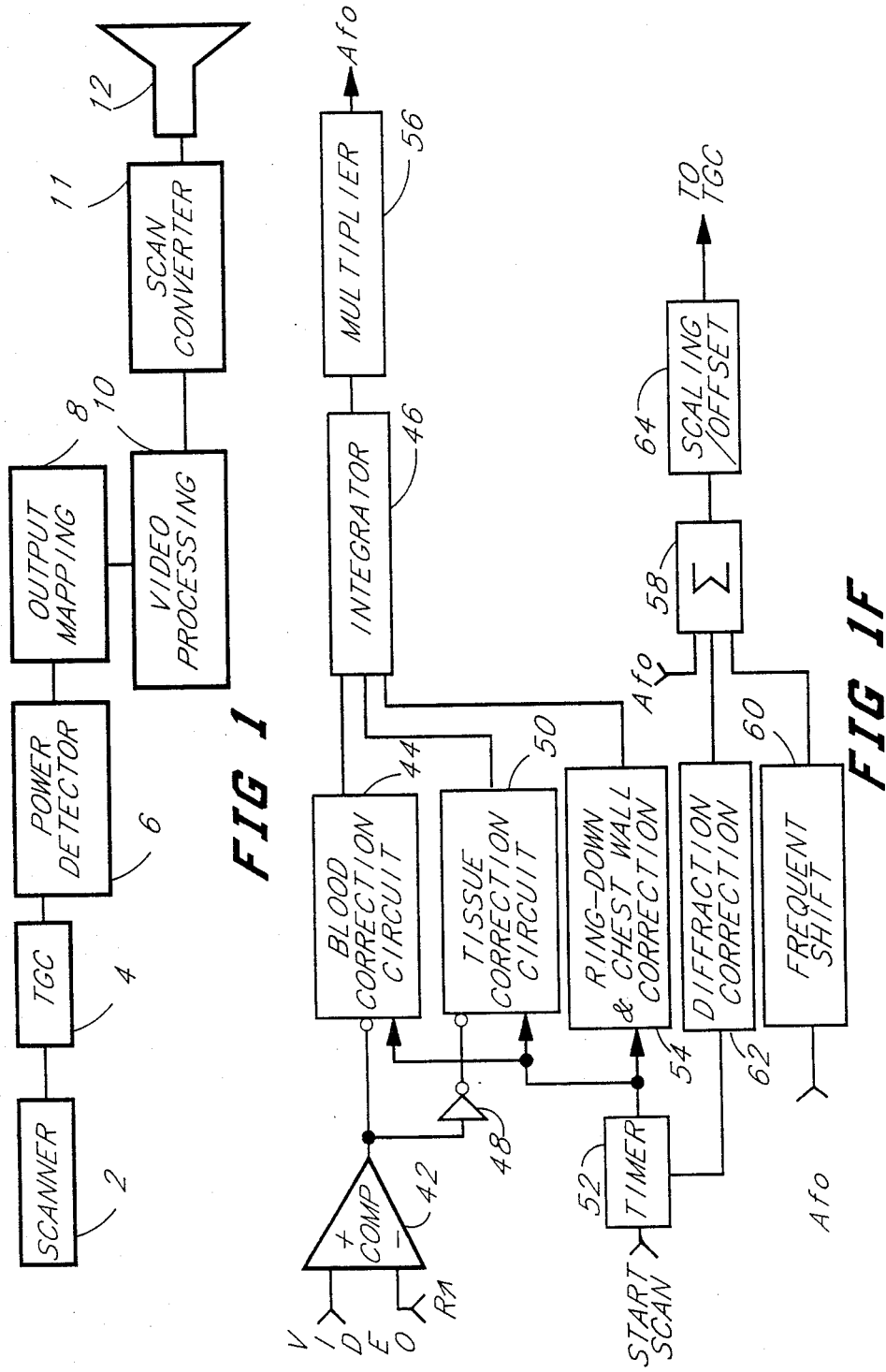

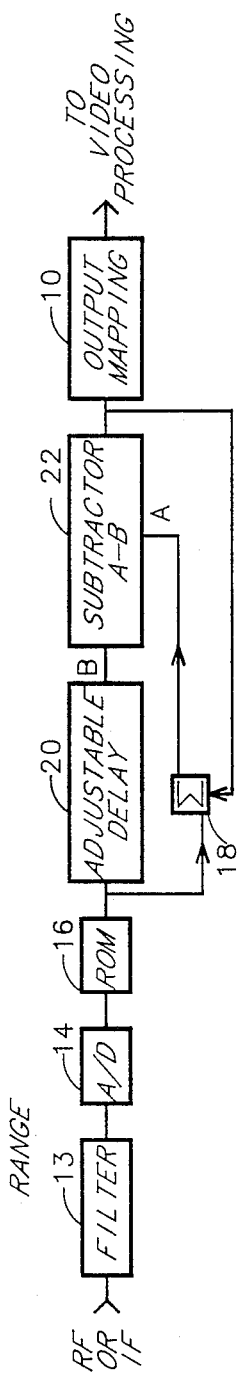
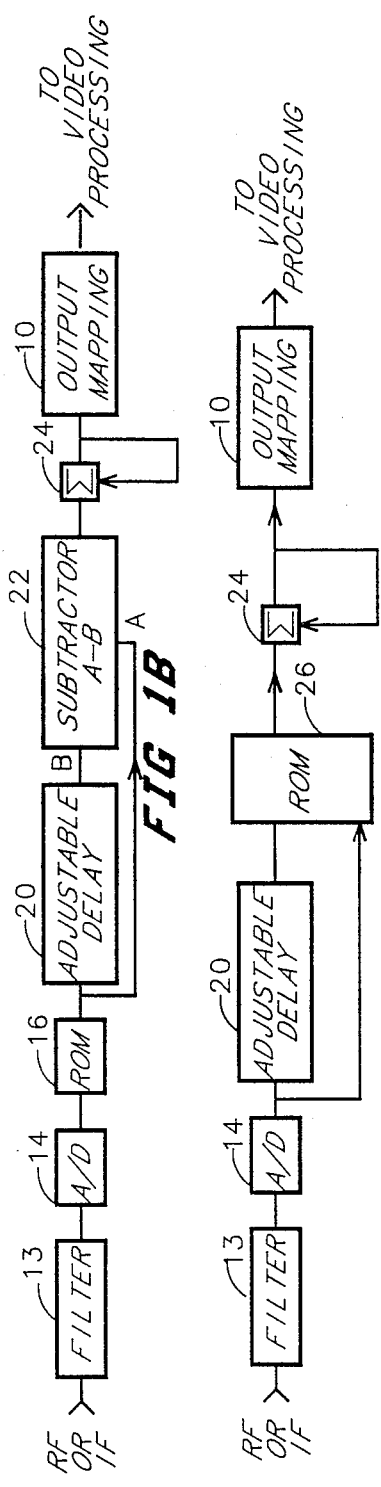

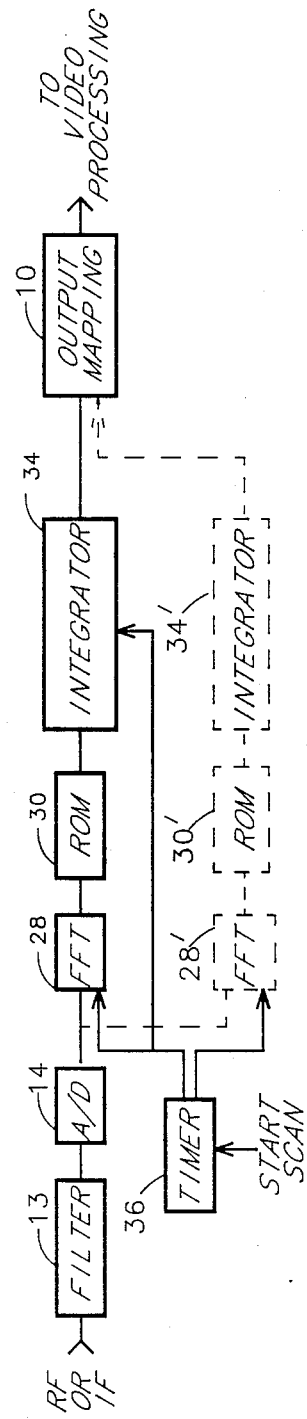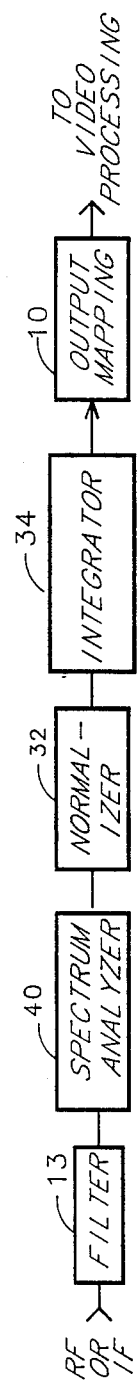

TECHNIQUES FOR CALCULATING ULTRASONIC INTEGRATED BACKSCATTER USING FREQUENCY OR TIME DOMAIN TECHNIQUES

BACKGROUND OF THE INVENTION

Systems that create two-dimensional images of structures within a body under examination by launching pulses of ultrasonic carrier waves into it along different radial paths and converting any echoes of the pulses into corresponding electrical waves have been commercially available for a number of years. The images thus formed have an intensity that is proportional to the amplitude of the echoes.

In an article entitled "Ultrasonic Characterization of Myocardium" in the September/October 1985 issue of *Progress in Cardiovascular Diseases,* the quantitative relationship between the energy of the backscatter of ultrasonic pressure waves and the condition of myocardium is discussed. Ischemic injury is of particular interest because its early detection would provide a real-time basis for determining whether or not a patient has had a heart attack as well as its extent, whereas present techniques for simply determining whether or not a heart attack has occurred often require several days of analysis. Although not discussed in the article, it is possible that other abnormal tissue conditions could be revealed by similar analysis. Whereas the article suggests the desirability of forming a two-dimensional image having intensity corresponding to the energy of the intensity of the echoes, no viable way of achieving this objective is described. The article does suggest that the variations in brightness of the images formed in response to the amplitude of echoes, as in the available apparatus briefly described above, can give some indication of the condition of the tissue, but the variations due to such phenomenon are so small that little reliance can be placed on them.

BRIEF SUMMARY OF THE INVENTION

In an article entitled "A Real-Time Integrated Backscatter Measurement System for Quantitative Cardiac Tissue Characterization", published in the January 1986 issue of *I.E.E.E. Transactions on Ultrasonics, Ferroelectrics and Frequency Control,* Vol. UFFC-33, No. 1, apparatus is described for deriving a signal corresponding to the power of backscatter from a pulse of ultrasonic carrier waves travelling along a single path. The apparatus described therein was wholly devised by two of the inventors of this invention. It converted the electrical carrier waves produced by a transducer in response to echoes impinging thereon to pressure waves which were applied to a cadmium sulphide crystal. Th CdS crystal produced an output corresponding to the power of the backscatter at all ranges. One of the limitations of this apparatus was its small dynamic range of about 20 db. No method of forming a two-dimensional image was described.

In accordance with a more practicable embodiment of this invention, an accurate two-dimensional image of the energy of backscatter may be formed in which a dynamic range of about 60 db is attained. Unprocessed electrical carrier waves produced by a transducer in response to backscatter or intermediate carrier waves derived therefrom are applied to a circuit for deriving a signal corresponding to the integration of the power of backscatter within a small range such as 2 mm. that runs along the path of the launched pulses. The circuit may derive the signal in either the frequency or time domain with adjustable integration ranges of frequency or time respectively. The signal may then directly modulate the intensity of a cathode ray beam so as to form an image corresponding in intensity to the energy of the backscatter or it may be processed by a scan converter before modulation of the cathode ray beam.

In view of the fact that the signal corresponds to energy, it is proportional to the square of the amplitude of the electrical carrier waves or electrical waves of intermediate frequency derived therefrom so that it is important that their amplitude be correct.

It is well known that the amplitude of echoes of launched pressure waves decreases with range so that it has been customary for apparatus forming an image of the amplitudes of echoes to employ a timed gain control circuit that increases the amplitude of the electrical carrier waves supplied by the transducer in response to the echoes received after each launched pulse.

Whereas this is satisfactory for images merely displaying the amplitudes of echoes, a gain control circuit used in a preferred form of this invention also provides a gain that changes less with time when the electrical waves result from echoes from blood than when the electrical waves result from echoes from myocardial tissue.

Greater accuracy is achieved if the gain control circuit causes zero gain during a period when ring-down of the transducer occurs following the transmit excitation. Additional accuracy is achieved if the gain control circuit compensates for echoes being received from the chest wall of the patient using a correction factor related to the chest wall attenuation as opposed to one related to myocardial tissue. In accordance with a further refinement, the gain control circuit introduces a component that reduces the gain as the range of echoes approaches the range where the launched beam is focussed and increases the gain thereafter. This is sometimes referred to as "diffraction correction". A still further refinement causes the gain control to compensate for the fact that the frequencies of which a launched pulse is comprised are attenuated by a factor proportional to frequency as the pulse travels through the body. This is sometimes referred to as "beam softening".

BRIEF DESCRIPTION OF THE DRAWINGS

FIG. 1 is a general block diagram of apparatus for producing a two-dimensional image of the energy of echoes in a supersonic system in accordance with this invention;

FIGS. 1A, 1B and 1C are block diagrams of respectively different circuits that operate in the time domain to derive the signal representative of the energy in the echoes;

FIGS. 1D and 1E are block diagrams of respectively different circuits that operate in the frequency domain to derive the signal representative of energy in the echoes;

FIG. 1F is a block diagram of a timed gain control circuit used in apparatus of the invention; and FIG. 1F' includes graphs illustrating diffraction correction.

DETAILED DESCRIPTION OF THE INVENTION

In FIG. 1, a scanner 2 contains a transducer means not shown for sequentially launching pulses of supersonic waves and converting any received echoes into corresponding electrical waves. A timed gain control circuit 4 varies the amplitudes of the electrical waves (as more fully described in connection with FIG. 1F) and applies them to a energy detector 6 that may be as illustrated in any one of FIGS. 1A through 1E. After being operated on by an output mapping circuit 8 that determines the brightness or color corresponding to the various amplitudes of the signal, and after suitable video processing has been accomplished by a video processor 10, the signal is applied so as to control the intensity or color of the image formed on a cathode ray tube 12.

In the following description of the various figures of the drawings, components having like functions have the same designations.

Reference is now made to a power detector of FIG. 1A that operates in a time domain. The electrical signals corresponding to echoes impinging on the transducer contained in the scanner 2 are passed through a normalizing filter 13 having an amplitude VS frequency characteristic largely determined by the transducer. They are then sampled by an A/D device 14, and its digital output is applied to the input of a ROM 16 that derives a digital signal representing the square of the amplitude of each sample. The digital word at the output of the ROM 16 is applied to one input of a summer 18 and to an input of an adjustable delay 20 that may be a FIFO shift register. An arithmetic logic unit 22 is coupled to the output of the summer 18 and to the output of the delay 20 so as to subtract the output of the delay 20 from the output of the summer 18. The output of the logic unit 22 is conneted to another input of the summer 18 as well as to an output mapping circuit 10, which is generally a ROM.

As each supersonic pulse is launched, all the devices in FIG. 1A are reset. Thus, if there are n steps in the FIFO delay 20, its output is zero for the first n samples of the A/D device 14, and the output of the logic unit 22 changes with each sample. When sample n+1 is taken, the output of the ROM 16 for the first sample appears at the output of the adjustable delay 20 and is subtracted from the old sum plus the square of sample n+1 so that the output of the logic unit 22 becomes the sum of the squares of the samples between 2 and n+1. Thus, the range represented by the signal at the output of the logic unit 22 is for n samples and equals the old sum of n−1 squared samples plus the squared value of the new sample.

In FIG. 1B, the output of the ROM 16 is directly connected to the input of the logic unit 22 to which the output of the summer 18 was connected in FIG. 1A, one input of a summer 24 is connected to the output of the logic unit 22, and the other input of the summer 24 is connected to its output. The mapping device 10 is connected to the output of the summer 24. Thus, the output of the logic unit 22 is the difference between the square of the current sample and the square of the $n^{th}$ previous sample so that the signal at the output of the summer 24 is the same as the signal at the output of the logic unit 22 of FIG. 1A.

In FIG. 1C, the ROM 16 for deriving the squares of the samples is eliminated, a portion of the address input of a different ROM 26 is connected to the output of the adjustable delay 20, and the remaining address bits of the ROM 26 are connected directly to the output of the A/D device 14. The bits at the output of the A/D device 14 and the bits at the output of the adjustable delay 20 combine to address a place in the ROM 26 where the difference of the squares is stored. The summer 24 derives a running sum of the squares of n samples as the signal for display.

The circuit illustrated in FIG. 1D operates in the frequency domain. The output of the A/D device 14 is connected to the input of a Fast Fourier Transform 28, and its output in turn is connected to a ROM 30 that derives the sum of the squares of the real and imaginary components for each frequency from the FFT 28. Since everything including noise is sampled by the A/D device 14, the output of the ROM 30 would include everything from DC to the Nyquist limit. An integrator 34 is provided that integrates over the usable bandwidth of the apparatus to provide the signal that is applied to the mapping means 10 to control the brightness and/or color of the image.

As described, the signal would be the integration of the squares of samples over some number of the frequency bins in the FFT and the FFT and the integrator 34 would have to be reset by a timer 36 after each range is completed. The timer 36 is started by a start-scan signal provided by the scanner 2 of FIG. 1. In order to provide overlapping rather than contiguous ranges, an FFT 28', a ROM 30' and an integrator 34' are connected as shown by the dashed lines, and the FFT 28' is started at some time during the range covered by the components shown in solid lines so as to cover a second range overlapping the first. A separate FFT, ROM and integrator would have to be supplied for each successive overlapping range, up to the number required to allow the first FFT, ROM and integrator to be available for another computation.

The circuit of FIG. 1E also operates in a frequency domain. The unprocessed electrical waves are applied to a spectrum analyzer 40 which may be a bank of filters, each of which is followed by a squaring circuit. The output of the analyzer 40 is normalized by a means 32. An integrator 34 integrates the output of the normalizer 32 over the usable bandwidth.

Reference is now made to the timed gain control circuit illustrated in FIG. 1F which provides a signal for controlling the gain of a device 4 (not shown) in the timed gain control device of FIG. 1. That device would ordinarily have a maximum gain that is reduced by the gain control signal so as to make the amplitude of the electrical waves supplied to the power detection device 6 of FIG. 1 the same as they would be if no attenuation were encountered.

The unprocessed video supplied by the power detector 6 of FIG. 1 may be applied to one input of a comparator 42, and a DC reference voltage R is applied to the other input. It would also be possible to apply unprocessed carrier or intermediate frequencies supplied by the scanner 2 to the non-inverting input of the comparator 42, but some means would have to be provided for preventing the comparator from undesirably changing state on successive half-cycles. The signals could be coupled to the non-inverting input via a properly poled diode or two one-shot multivibrators could be connected in tandem to the output of the comparator 42. When the electrical signals result from back-scatter from tissue, each positive half-cycle will cause the comparator 42 to go high; but when the electrical waves result from backscatter from blood, they have less amplitude and do not exceed the reference voltage R so that the output of the comparator 42 is low. A blood correction circuit 44 that, when enabled, supplies a given DC voltage to one input of an integrator 46 is connected to the output of the comparator 42. The blood correction circuit 44 is such that it is enabled when the output of the comparator 42 is low or zero.

An inverter 48 is connected between the output of the comparator 42 and an enabling input of a tissue correction circuit 50 that, when enabled by a low state, supplies a DC voltage, which may be different than that supplied by the blood correction circuit 44, to an input of the integrator 46. The tissue correction circuit 50 can be made to provide different DC voltages depending on the orientation of the tissue fibers in a manner to be described in a subsequent patent application. When the electrical signals result from backscatter from tissue, the tissue correction circuit is operative.

The reference voltage R can be adjusted while observing the image on the cathode ray tube 12. If R is set too high, the output of the comparator 42 remains low so that only the blood correction circuit 44 is enabled even if the echoes are from tissue. In this case, the increase in gain with time is less than it should be to compensate for the passage of the pulses through tissue so that the scatter from tissue has less amplitude than it should have and the image is dark. If R is set too low, the output of the comparator 42 remains high so that only the tissue correction circuit 50 is enabled even if the echoes are from blood. In this case, the increase in gain with time is greater than it should be to compensate for the passage of the pulses through blood so that the scatter from blood has greater amplitude than it should have and the image is bright. If the display is in color or combination of color and brightness, the effects of too high or too low a value of R will cause different effects that can be recognized.

A timing circuit 52 that is synchronized by a start-scan signal from the scanner 2 of FIG. 1 supplies a signal to a ring-down and chest wall correction circuit 54 that enables it for the first several microseconds after the launching of a pulse and disables the blood correction circuit 44 and the tissue correction circuit 50. During the first few microseconds during which the transducer of the scanner 2 is ringing down, the circuit 54 applies a zero voltage to an input of the integrator 46; and during the next few microseconds, corresponding to propagation through the chest wall, it supplies a DC voltage to an input of the integrator 46 appropriate to compensate for attenuation in the chest wall.

A multiplier 56, which may be a gain selectable amplifier, multiplies the output A of the integrator 46 with a DC voltage fo that is proportional to the carrier frequency of the launched pulses so as to derive a term Afo which is supplied to one input of a summer 58.

The signal Afo is also supplied to a frequency shift or beam softening correction circuit 60 which supplies a DC voltage to an input of the summer 58 that changes proportionally to $fo^2$. This is to compensate for the fact that attenuation increases with frequency so that the higher frequencies of a launched pulse are attenuated more than the lower frequencies, thereby effectively shifting the center frequency of an echo below the center frequency of a launched pulse.

A diffraction correction circuit 62 that is enabled by a pulse from the timer 52 supplies a voltage to the summer 58 that compensates for the fact that the echoes have a maximum amplitude when they are backscattered from reflectors at the focal point of the launched beam of pulses and a gradually decreasing amplitude as the range increases or decreases from the focal point. Thus, as indicated in FIG. 1F', the amplitude A of backscatter from like objects varies with range as indicated by the solid line A, and the gain required for compensation is indicated by the reciprocal curve G, all of which is negative.

The DC voltage at the output of the summer 58 is applied to a circuit 64 for scaling and offset adjustment, i.e., if the gain control signal is to run between zero and $-5$ volts in order to swing the gain of the timed gain control circuit 4 of FIG. 1 from zero to a maximum, the output voltage of the summer 58 is adjusted accordingly so as to have the right polarity and amplitude range.

Whereas most supersonic equipment uses the same transducer for launching pulses and receiving echoes, the term "backscatter" is used but, as used herein, that term is meant to apply to scatter in any direction. Thus, the means for launching pulses may be at one point on the body and the means for receiving the echoes may be at another point because backscatter or scatter goes in all direction. It is only necessary to process the scatter or backscatter from locations along a plurality of known paths.

What is claimed is:

1. Apparatus for deriving signals indicative of the integrated ulrasonic backscatter of tissue lying along lines in a cross sectional area of a body comprising:
   means for respectively launching pulses of ultrasonic pressure waves along a plurality of lines in a cross sectional area of a body in sequence,
   transducer means for continually deriving first electrical signals from pressure waves scattered by tissues lying along each line,
   circuit means responsive to said first electrical signals for continuously producing second electrical signals representing the instanteous ultrasonic power scattered by the tissue, and
   circuit means for continuously integrating said second signals as they are produce so as to obtain third signals representing the ultrasonic energy scattered by a given volume of tissue that moves outward along said lines after a pulse is launched.

2. Apparatus for deriving an integrated backscatter signal indicative of the integrated backscatter of tissue lying along lines passing through a cross sectional area of a body comprising:
   means for respectively launching pulses of ultrasonic pressure waves in sequence along a plurality of lines extending through said cross sectional area,
   means responsive to reflections of the pulses of pressure waves for producing electrical signals,
   sampling means for deriving samples corresponding to the amplitude of said electrical waves at successive times,
   arithmetic means coupled to said sampling means for deriving the square of ecah sample,
   a summer having two inputs and an output, one input being coupled to the output of said arithmetic means,
   a FIFO delay coupled to the output of said arithmetic means,
   a subtractor for subtracting a signal applied to a first input thereof from a signal applied to a second input thereof, said first input being coupled to said FIFO delay and said second input being coupled to the output of said summer, and the output of said subtractor being coupled to the other input of said summer, whereby said signal indicative of backscatter appears at the output of said subtractor.

3. Apparatus for deriving an integrated backscatter signal indicative of the integrated backscatter of tissue lying along lines passing through a cross sectional area of a body comprising:

means for respectively launching pulses of ultrasonic pressure waves in sequence along a plurality of lines extending through said cross sectional area, means responsive to reflections of the pulses of pressure waves for producing electrical signals, sampling means for deriving samples respectively corresponding to amplitude of said electrical waves at successive times, arithmetic means coupled to the output of said sampling means for deriving the square of each sample, a subtractor for subtracting a signal applied to a first input thereof from a signal applied to a second input thereof, said second input being coupled to the output of said arithmetic means, a FIFO delay coupled between said arithmetic means and said first input of said subtractor, and a summer having one input coupled to the output of said subtractor and an output coupled to another input of said subtractor whereby said signal indicative of backscatter appears at the output of said summer.

4. Apparatus for deriving an integrated backscatter signal indicative of the integrated backscatter of tissue lying along lines passing through a cross sectional area of a body comprising:

means for respectively launching pulses of ultrasonic pressure waves in sequence along a plurality of lines extending through said cross sectional area, means responsive to reflections of the pulses of pressure waves for producing electrical signals, sampling means for deriving samples respectively corresponding to the amplitude of the said electrical waves at successive times, computation means having first and second inputs and an output, said computation means providing at its output a signal equal to the square of a signal applied to its first input less the square of a signal apllied to its second input, said first input being coupled to the output of said sampling means, a FIFO delay coupled between said sampling means and said second input of said computation means, and a summer having first and second inputs and an output, said first input being coupled to the output of said computation means and said second input being coupled to said output of said summer whereby said signal indicative of backscatter appears at the output of said summer.

5. Apparatus for deriving an integrated backscatter signal indicative of the integrated backscatter of tissue lying along lines passing through a cross sectional area of a body comprising:

means for respectively launching pulses of ultrasonic pressure waves in sequence along a plurality of lines extending through said cross sectional area, means responsive to reflections of the pulses of pressure waves for producing electrical signals, sampling means for deriving samples respectively corresponding to the amplitude of said electrical waves at successive times, an FFT circuit coupled to said sampling means, said FFT circuit supplying real and imaginary components of each of a plurality of frequencies represented by said samples, arithmetic means for deriving signals equal to the sum of the squares of each of said real and imaginary components appearing at the output of said FFT circuit, an integrator for integrating the signals at the output of said arithmetic means over the usable bandwidth of the frequency components at the output of said FFT circuit whereby said signal representing backscatter for the integrated backscatter of a given range appears at the output of said integrator, and means for resetting said FFT circuit and said integrator after a given number of samples have been derived by said sampling means.

6. Apparatus as set forth in claim 5 further comprising:

a second FFT circuit coupled to said sampling means, a second arithmetic means and a second integrator connected in series to said second FFT circuit so as to derive said signal representing backscatter for a different range, and means for resetting said second FFT circuit and said second integrator before said first mentioned FFT circuit and said first mentioned integrator have been reset.

7. Apparatus for deriving an integrated backscatter signal indicative of the integrated backscatter of tissue lying along lines passing through a cross sectional area of a body comprising:

means for respectively launching pulses of ultrasonic pressure waves in sequence along a plurality of lines extending through said corss sectional area, means responsive to reflections of the pulses of pressure waves for producing electrical signals, a spectrum analyzer having means for providing the square of the amplitude of each of a plurality of frequency components of said electrical waves, and an integrator coupled to the output of said spectrum analyzer whereby said signal representing backscatter appears at the output of said integrator.

* * * * *

UNITED STATES PATENT AND TRADEMARK OFFICE
CERTIFICATE OF CORRECTION

PATENT NO. : 4,873,984

DATED : 10/17/89

INVENTOR(S) : Thomas J. Hunt, James G. Miller, Lewis J. Thomas III, Hewlett E. Melton, and Thomas A. Shoup It is certified that error appears in the above-identified patent and that said Letters Patent is hereby corrected as shown below:

Column 3, line 37, "conneted" should read — connected —;

Column 6, line 60, "ecah" should read — each —;

Column 7, line 50, "apllied" should read — applied —;

Column 8, line 49, "corss" should read — cross —;

Title Page:

Item [73] Assignee: "Hewlett-Packard Company, Palo Alto, CA" should read --Washington University, St. Louis, MO--.

Signed and Sealed this

Seventh Day of January, 1992

*Attest:*

HARRY F. MANBECK, JR.

*Attesting Officer*     *Commissioner of Patents and Trademarks*